US010182724B2

(12) United States Patent
Mak et al.

(10) Patent No.: US 10,182,724 B2
(45) Date of Patent: *Jan. 22, 2019

(54) OPTICAL COHERENCE TOMOGRAPHY SYSTEM INCLUDING A PLANARIZING TRANSPARENT MATERIAL

(71) Applicant: SYNAPTIVE MEDICAL (BARBADOS) INC., Bridgetown (BB)

(72) Inventors: Siu Wai Jacky Mak, Toronto (CA); Michael Frank Gunter Wood, Toronto (CA)

(73) Assignee: SYNAPTIVE MEDICAL (Barbados) Inc., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/890,801

(22) Filed: Feb. 7, 2018

(65) Prior Publication Data

US 2018/0177400 A1 Jun. 28, 2018

Related U.S. Application Data

(63) Continuation of application No. 15/500,961, filed as application No. PCT/IB2015/051618 on Mar. 5, 2015, now Pat. No. 9,924,871.

(51) Int. Cl.
*A61B 5/00* (2006.01)
*A61B 34/20* (2016.01)
(Continued)

(52) U.S. Cl.
CPC ............ *A61B 5/0066* (2013.01); *A61B 5/065* (2013.01); *A61B 17/0206* (2013.01);
(Continued)

(58) Field of Classification Search
CPC ............ A61B 5/0066; A61B 1/00087; A61B 1/00096; A61B 1/00101; A61B 2017/0034
See application file for complete search history.

(56) References Cited

U.S. PATENT DOCUMENTS 6,458,079 B1 * 10/2002 Cohn .................... A61B 17/02
600/210
7,706,646 B2 * 4/2010 Wang ................... A61B 5/0062
362/572

(Continued)

FOREIGN PATENT DOCUMENTS

EP 2312997 A1 4/2011
WO WO-2014085911 A1 6/2014

OTHER PUBLICATIONS

International Search Report dated Dec. 3, 2015 for International Patent Application No. PCT/IB2015/051618.
(Continued)

*Primary Examiner* — Angela M Hoffa
(74) *Attorney, Agent, or Firm* — Perry + Currier Inc.

(57) ABSTRACT

An optical coherence tomography ("OCT") system that includes a planarizing transparent material is provided. The OCT system comprises: an OCT probe comprising: a body having a distal end and a proximal end; a positioner adapter located at the proximal end; a connector to an OCT analysis device, the connector located at the proximal end; and, an OCT scan lens located at the distal end; and, a transparent material configured to planarize tissue at a scan plane of the OCT scan lens.

16 Claims, 15 Drawing Sheets

(51) Int. Cl.
*A61B 17/02* (2006.01)
*A61B 5/06* (2006.01)
*A61B 90/00* (2016.01)
*A61B 17/00* (2006.01)
*A61B 90/20* (2016.01)

(52) U.S. Cl.
CPC .......... *A61B 17/0218* (2013.01); *A61B 34/20* (2016.02); *A61B 90/39* (2016.02); *A61B 90/20* (2016.02); *A61B 2017/00907* (2013.01); *A61B 2034/2051* (2016.02); *A61B 2034/2055* (2016.02); *A61B 2034/2072* (2016.02); *A61B 2090/3735* (2016.02); *A61B 2090/3937* (2016.02)

(56) References Cited

U.S. PATENT DOCUMENTS

| | | | | |
|---|---|---|---|---|
| 7,736,308 | B2* | 6/2010 | Cohn | A61B 17/02 128/852 |
| 8,041,162 | B2* | 10/2011 | Wang | A61B 5/0062 362/572 |
| 8,346,346 | B1* | 1/2013 | Schnitzer | A61B 1/043 600/175 |
| 8,409,083 | B2* | 4/2013 | Mangiardi | A61B 17/02 600/184 |
| 8,608,650 | B2* | 12/2013 | Mangiardi | A61B 17/02 600/184 |
| 8,666,209 | B2* | 3/2014 | Wang | A61B 5/0062 362/572 |
| 9,161,694 | B2* | 10/2015 | Schnitzer | A61B 1/043 |
| 9,186,175 | B2* | 11/2015 | Mark | A61B 1/0607 |
| 9,307,969 | B2* | 4/2016 | Novak | A61B 17/02 |
| 9,566,052 | B2* | 2/2017 | Novak | A61B 17/02 |
| 9,579,121 | B2* | 2/2017 | Mark | A61B 17/3468 |
| 9,622,777 | B2* | 4/2017 | Mark | A61B 17/3423 |
| 9,924,871 | B2* | 3/2018 | Mak | A61B 5/0066 |
| 2003/0013941 | A1* | 1/2003 | Cohn | A61B 17/02 600/213 |
| 2004/0092804 | A1* | 5/2004 | Rebec | A61B 5/14532 600/310 |
| 2008/0021276 | A1* | 1/2008 | Wax | A61B 1/00096 600/122 |
| 2008/0267562 | A1* | 10/2008 | Wang | A61B 5/0062 385/31 |
| 2009/0177094 | A1* | 7/2009 | Brown | A61B 5/0066 600/476 |
| 2010/0201985 | A1* | 8/2010 | Wang | A61B 5/0062 356/369 |
| 2011/0105848 | A1* | 5/2011 | Sadovsky | A61B 17/0218 600/204 |
| 2011/0261353 | A1* | 10/2011 | Teramura | A61B 1/00096 356/213 |
| 2012/0033911 | A1* | 2/2012 | Wang | A61B 5/0062 385/11 |
| 2012/0059225 | A1* | 3/2012 | Gostout | A61B 1/32 600/204 |
| 2012/0071748 | A1* | 3/2012 | Mark | A61B 17/3421 600/411 |
| 2012/0149992 | A1* | 6/2012 | Duggal | A61B 17/02 600/245 |
| 2012/0253375 | A1* | 10/2012 | Mark | A61B 1/0607 606/185 |
| 2012/0289816 | A1* | 11/2012 | Mark | A61M 39/0247 600/411 |
| 2013/0102851 | A1* | 4/2013 | Mark | A61B 17/3468 600/233 |
| 2014/0187922 | A1* | 7/2014 | Mark | A61B 5/064 600/424 |
| 2014/0221826 | A1* | 8/2014 | Joos | A61B 5/0066 600/425 |
| 2015/0109427 | A1* | 4/2015 | Wood | A61B 1/043 348/68 |
| 2016/0015476 | A1* | 1/2016 | Jagga | A61B 42/10 606/1 |
| 2016/0038253 | A1* | 2/2016 | Piron | A61B 19/56 600/424 |
| 2016/0095623 | A1* | 4/2016 | Mark | A61B 1/0607 600/424 |
| 2016/0113728 | A1* | 4/2016 | Piron | A61B 17/3421 606/130 |
| 2016/0324664 | A1* | 11/2016 | Piron | A61F 2/46 |
| 2017/0079529 | A1* | 3/2017 | Mak | A61B 5/00 |
| 2017/0143429 | A1* | 5/2017 | Richmond | A61B 34/20 |
| 2017/0215733 | A1* | 8/2017 | Mak | A61B 5/0066 |

OTHER PUBLICATIONS

Written Opinion dated Dec. 3, 2015 for International Patent Application No. PCT/IB2015/051618.
International Preliminary Report on Patentability dated Jan. 11, 2017 for PCT International Application No. PCT/IB2015/051618.
Non-Final Rejection dated Jun. 7, 2017 for U.S. Appl. No. 15/500,961.

\* cited by examiner

OPTICAL COHERENCE TOMOGRAPHY SYSTEM INCLUDING A PLANARIZING TRANSPARENT MATERIAL

FIELD

The specification relates generally to optical coherence tomography and methods for minimally invasive therapy and image guided medical procedures, and specifically to an optical coherence tomography system that includes a planarizing transparent material.

BACKGROUND

Optical Coherence Tomography (OCT) enables imaging of tissue with depth limited to typically 1-2 mm due to the light absorption and scattering property of tissue. When the object being imaged lies outside, but closed to, the range of imaging depth (i.e. the 1-2 mm mentioned above), the OCT image of the object could lie outside of the image (i.e. image could not be shown). On the other hand, the OCT image could be shown upside down overlapping with part of the object that lies within the imaging depth. This is known as a mirror artifact. In addition, optimal wavelengths for OCT imaging on turbid tissue, such as the brain, lies in the near-infrared range which is not visible to the human eye. As a result, surgeons and/or users performing the imaging cannot see the exact scanning area and the laser spot size. This makes focusing, position and alignment of the OCT probe or scanning head difficult. A visible laser could be coupled into the OCT system showing the scanning area on the object. However, this additional laser is added with performance lost in the system such as power loss, increased optical noise, and reduced bandwidth. System cost also increases as a result because wavelength division multiplexing unit is required to couple both the visible and NIR (near infrared) light into the same optical path.

SUMMARY

The present disclosure is generally directed to image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Further, an OCT system is provided which includes an OCT probe and a transparent material configured to planarize tissue at a scan plane of the OCT scan lens, which may assist in reducing and/or eliminating mirror artifacts in OCT scan images. The transparent material may be at an offset distance from the OCT scan lens of the OCT probe, and the OCT probe may further comprise apparatus for maintaining the offset distance between the OCT scan lens and the transparent material. As the transparent material may also define the scan area, a need for use of a laser to visualize the scan area may be obviated. The OCT probe may further be tracked in a three dimensional space using a NIR navigation system through the addition of a tracking device onto the OCT probe and/or a device positioner in which the OCT probe is mounted on. The transparent material may define the scan area may mayalso be a separate component from the rest of the OCT probe. In this configuration, an OCT probe, comprising the transparent material, a handle and a tracking device, may be included for automated positioning and focusing of a scan probe to scan the area-of-interest.

An aspect of the present specification provides an OCT (Optical Coherence Tomography) system comprising: an OCT probe comprising: a body having a distal end and a proximal end; a positioner adapter located at the proximal end; a connector to an OCT analysis device, the connector located at the proximal end; and, an OCT scan lens located at the distal end; and, a transparent material configured to planarize tissue at a scan plane of the OCT scan lens.

The transparent material may be substantially transparent to light used in optical coherence tomography.

The OCT system of claim 1, wherein the OCT probe and the transparent material are discrete components. The OCT system may further comprise a handle attached to the transparent material. The handle may be configured to extend through a surgical port. The handle may be configured to be held by a human hand. The OCT probe may further comprise a tracking device located at a respective proximal end of the handle, the tracking device configured to be tracked by a navigation system.

A tissue-facing side of the transparent material may be substantially flat.

The OCT system may further comprise one or more of an immersion material and an index matching material on a tissue-facing side of the transparent material, the one or more of the immersion material and the index matching material configured to optically couple the transparent material to the tissue.

A side of the transparent material facing the OCT scan lens may be at an angle to a surface of the OCT scan lens.

A distance between the OCT scan lens and the scan plane may comprise an OCT scan distance.

The transparent material may extend between the OCT scan lens and the scan plane.

The OCT system may further comprise an offset device, the transparent material may be located at the scan plane, and the offset device may be configured to maintain an offset distance between the OCT scan lens and the transparent material. The OCT system may further comprise space between the transparent material and the OCT scan lens. The offset device may comprise a frame configured to hold the transparent material at the offset distance.

The transparent material may comprise glass.

The transparent material may comprise plastic.

The positioner adapter may be configured to be held by a human hand.

The positioner adapter may be configured to be held by an arm of a surgical system. The arm of the surgical system may be configured to position the body relative to the tissue.

The body may be configured for insertion through a surgical port configured for corridor based surgery.

The OCT system may further comprise a tracking device located at the proximal end, the tracking device configured to be tracked by a navigation system.

The OCT system may further comprise: a navigation system; a first tracking device located at the proximal end, the first tracking device configured to be tracked by the navigation system; a handle attached to the transparent material, the OCT probe and the transparent material being one or more of discrete components and separate components, the handle configured to be held by a human hand; a second tracking device located a respective proximal end of the handle, the second tracking device configured to be tracked by the navigation system; and, a device positioner configured to hold the OCT probe, the device positioner in communication with the navigation system, the device positioner configured to position the OCT probe relative to the transparent material as the navigation system tracks respective positions of the first tracking device and the second tracking device.

BRIEF DESCRIPTIONS OF THE DRAWINGS

For a better understanding of the various implementations described herein and to show more clearly how they may be carried into effect, reference will now be made, by way of example only, to the accompanying drawings in which.

Figure 6:
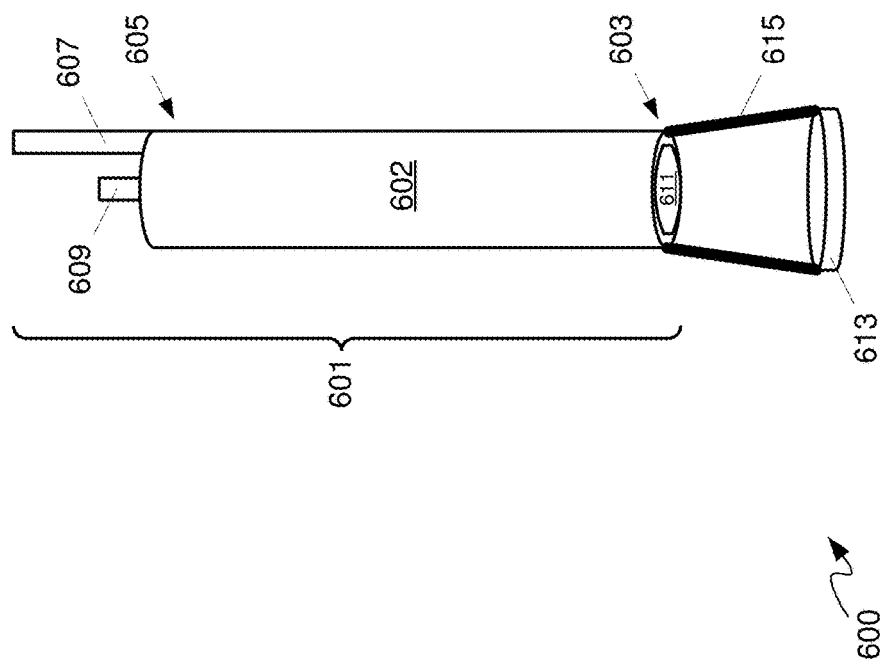
FIG. 6 depicts an OCT (Optical Coherence Tomography) system, according to non-limiting implementations.
Figure 7:
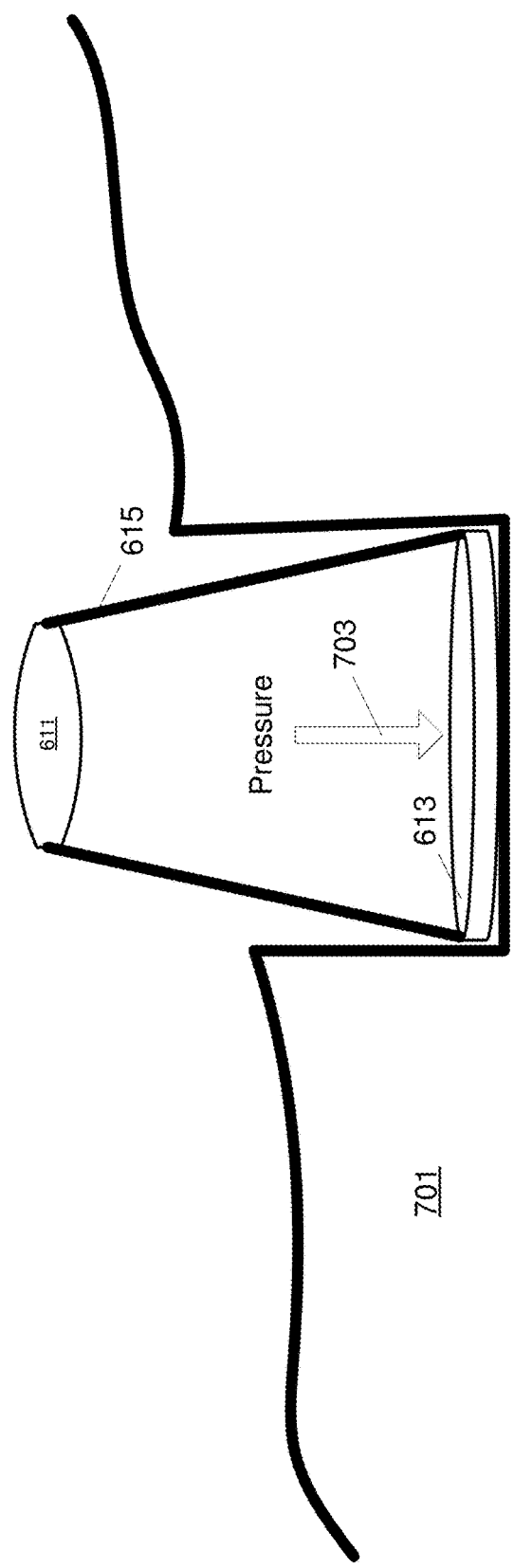

FIG. 7 components of the OCT system of FIG. 6 in use with tissue, according to non-limiting implementations.

Figure 8:
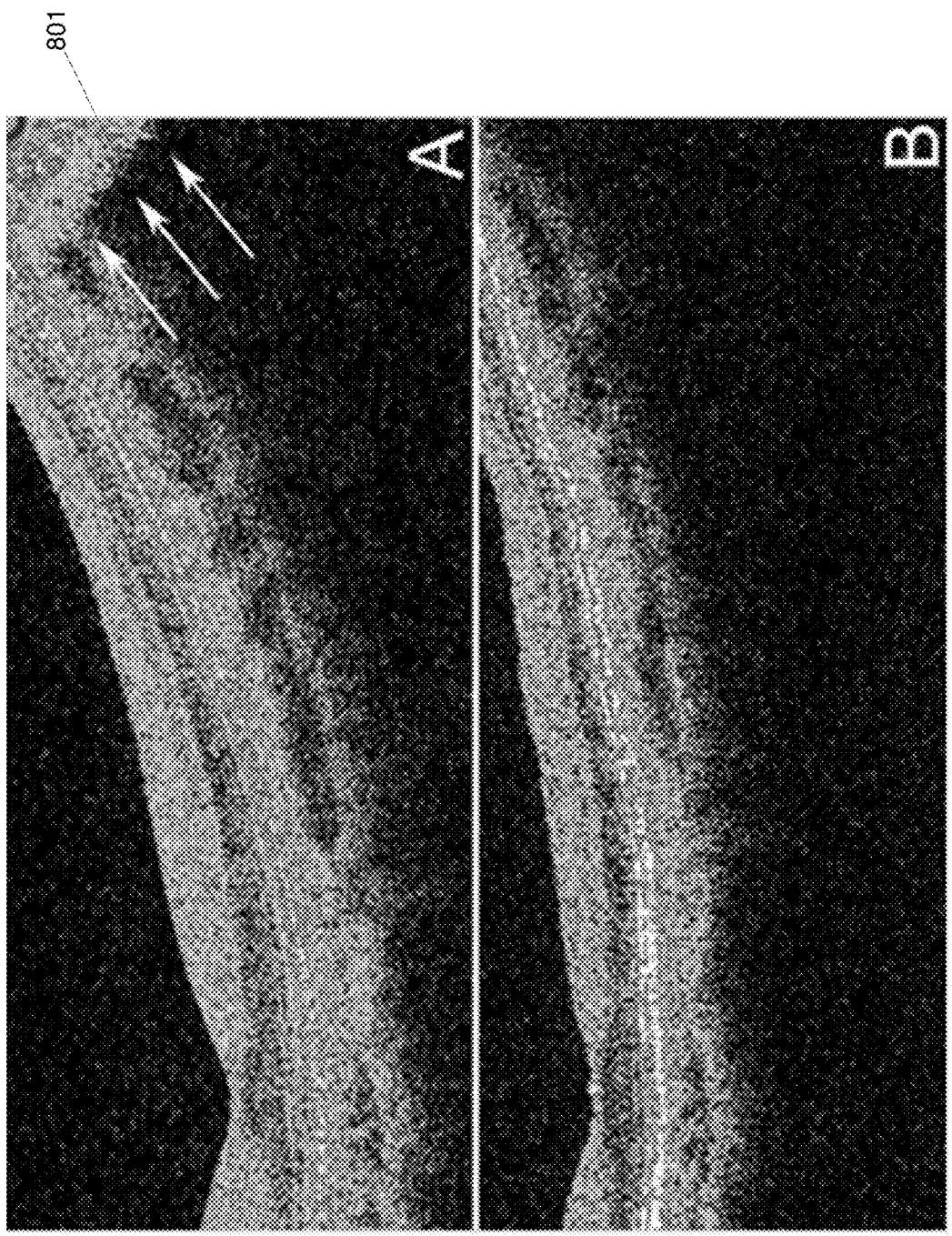

FIG. 8 depicts OCT images acquired without and with planarized tissue, according to non-limiting implementations.

Figure 9:
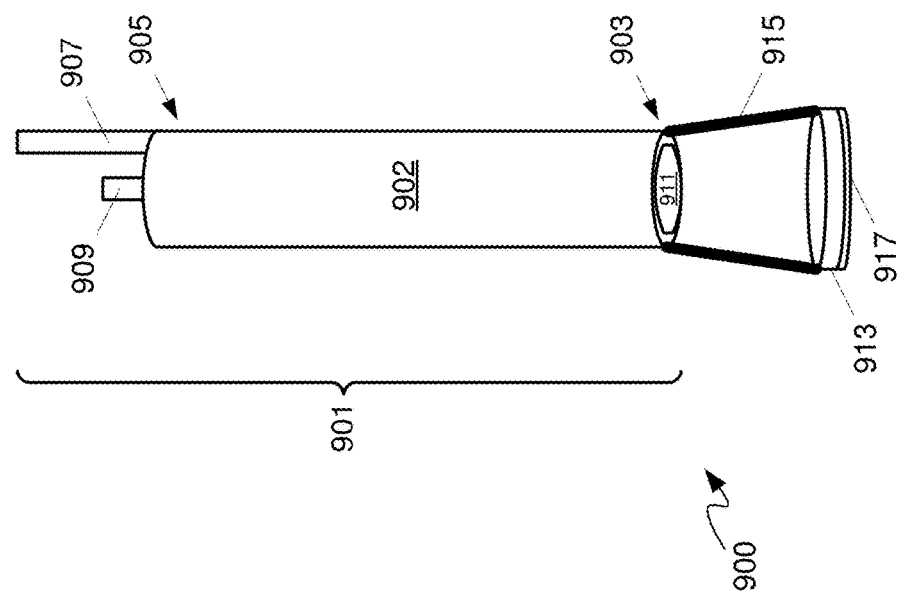

FIG. 9 depicts an OCT system that includes one or more of an immersion material and an index matching material, according to alternative non-limiting implementations.

Figure 10:
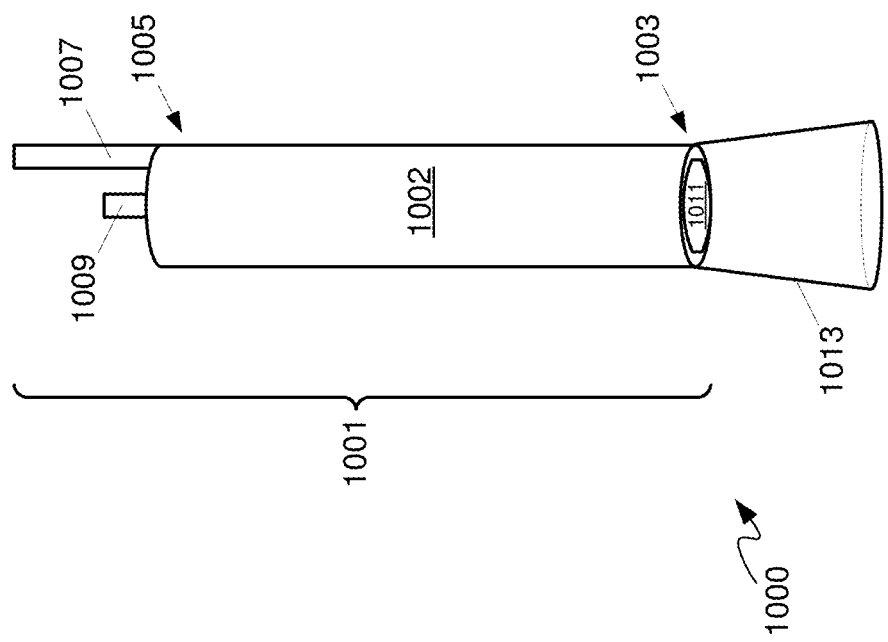

FIG. 10 depicts an OCT system that includes a transparent material that extends from an OCT scan lens to an OCT scan plane, according to alternative non-limiting implementations.

Figure 11:
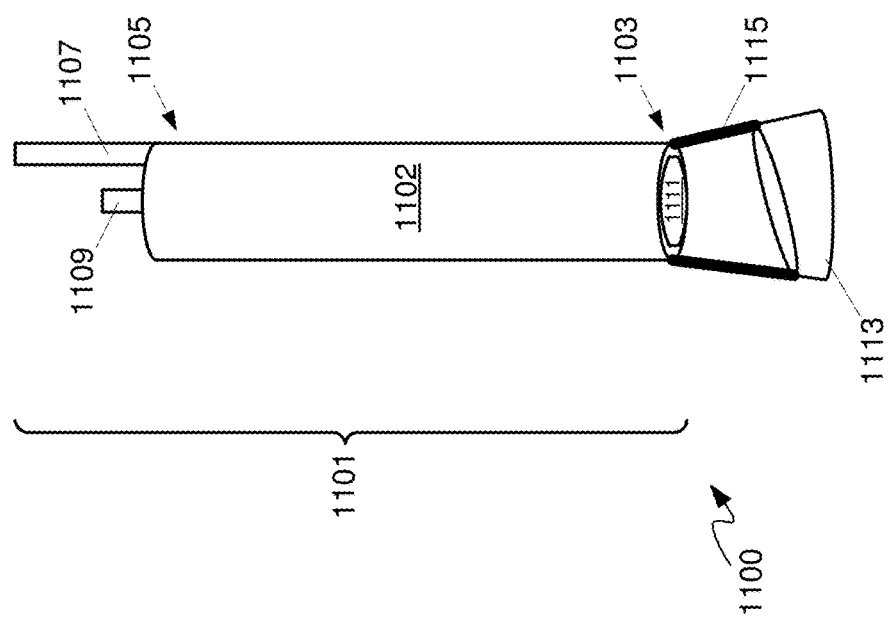

FIG. 11 depicts an OCT system that includes a transparent material with an angled side relative to an OCT scan lens and/or an OCT scan plane, according to alternative non-limiting implementations.

Figure 12:
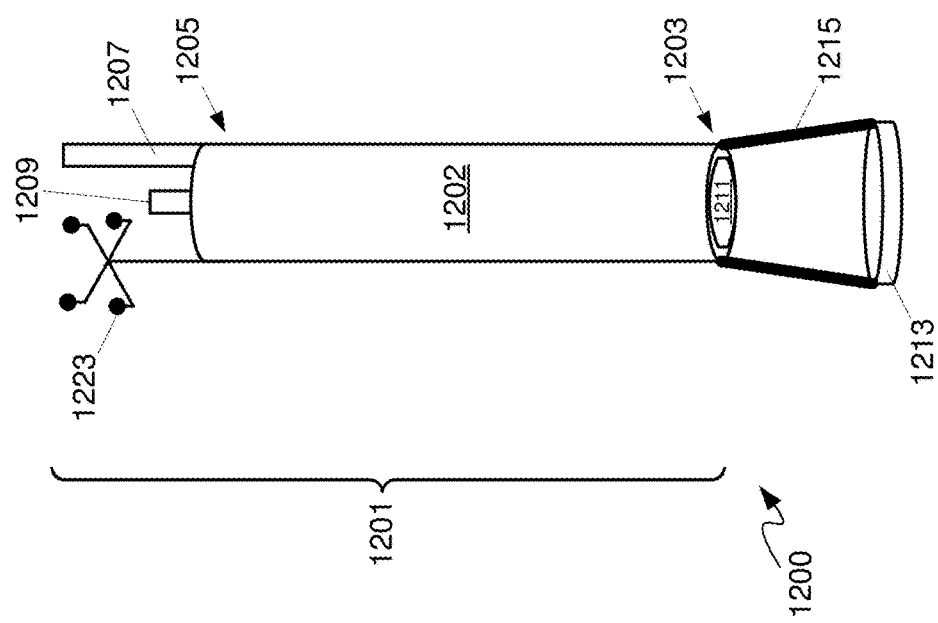

FIG. 12 depicts an OCT system that includes a tracking device, according to alternative non-limiting implementations.

Figure 13:
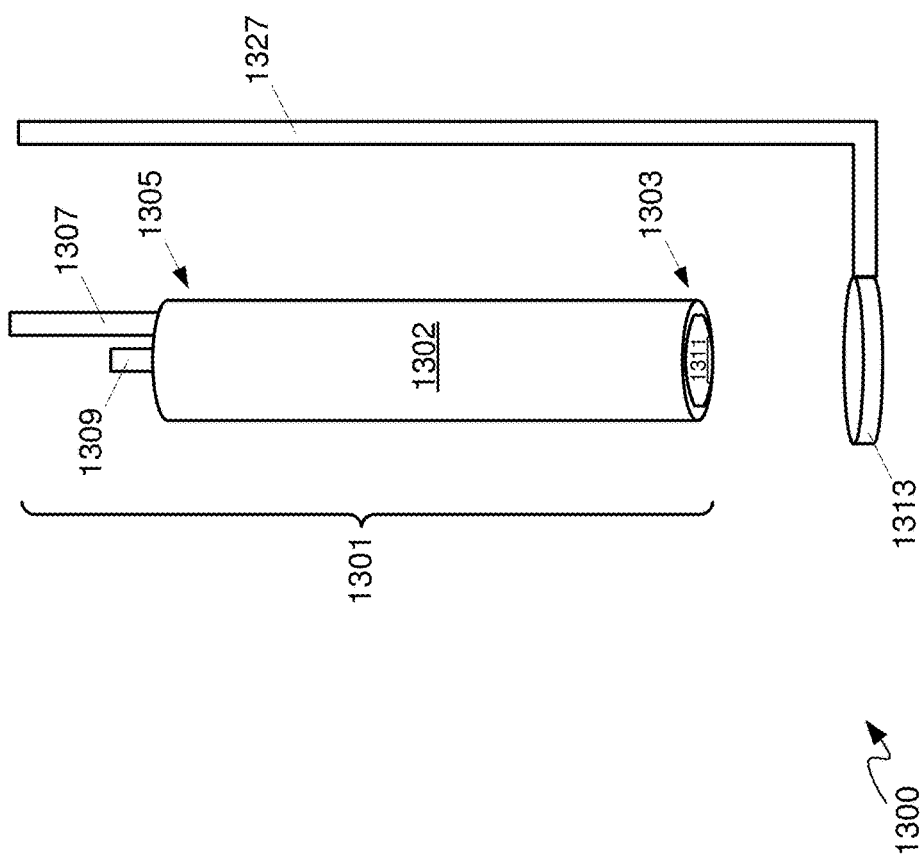

FIG. 13 depicts an alternative implementation of an OCT system in which the OCT probe and the transparent material are discrete components.

Figure 14:
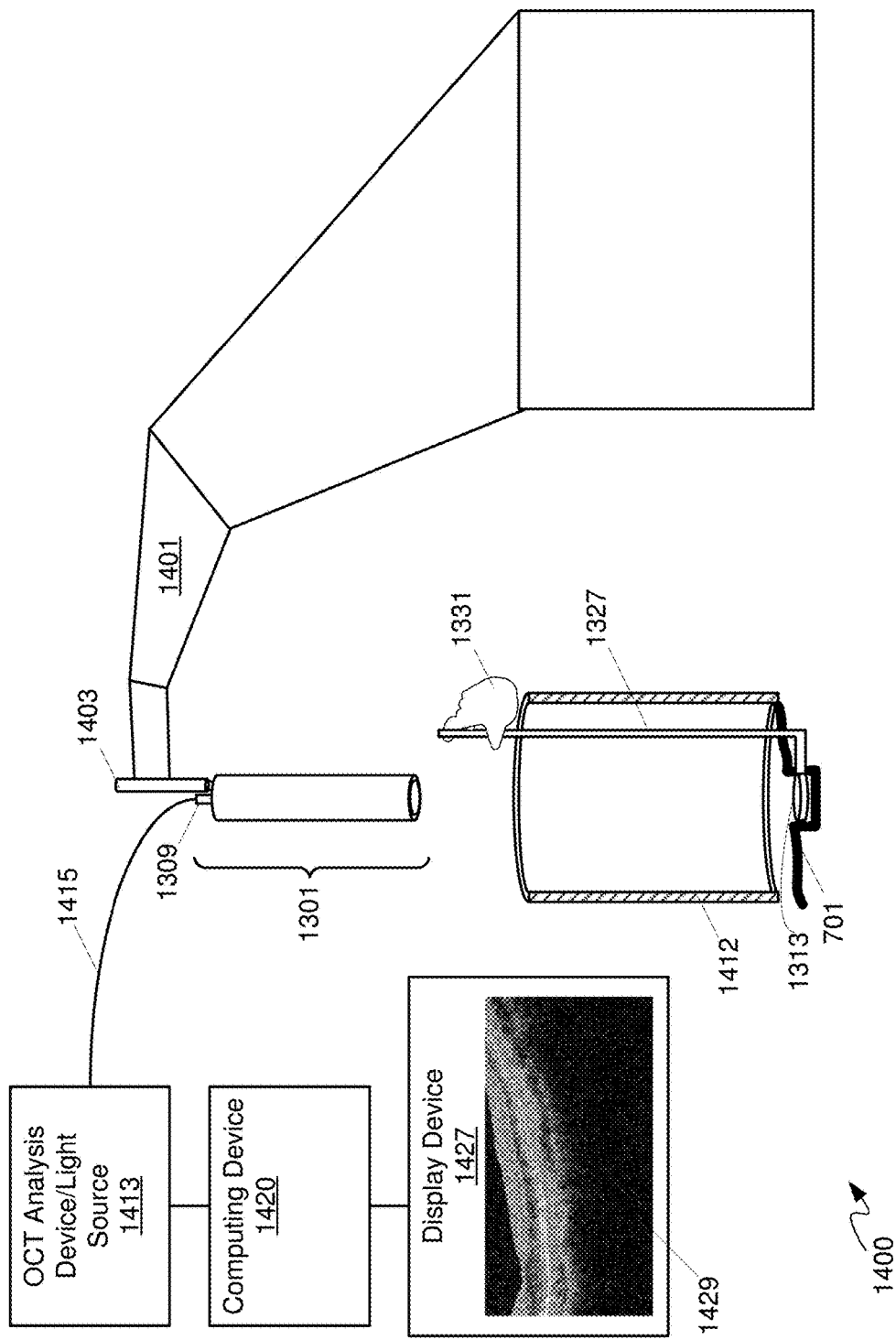
Figure 15:
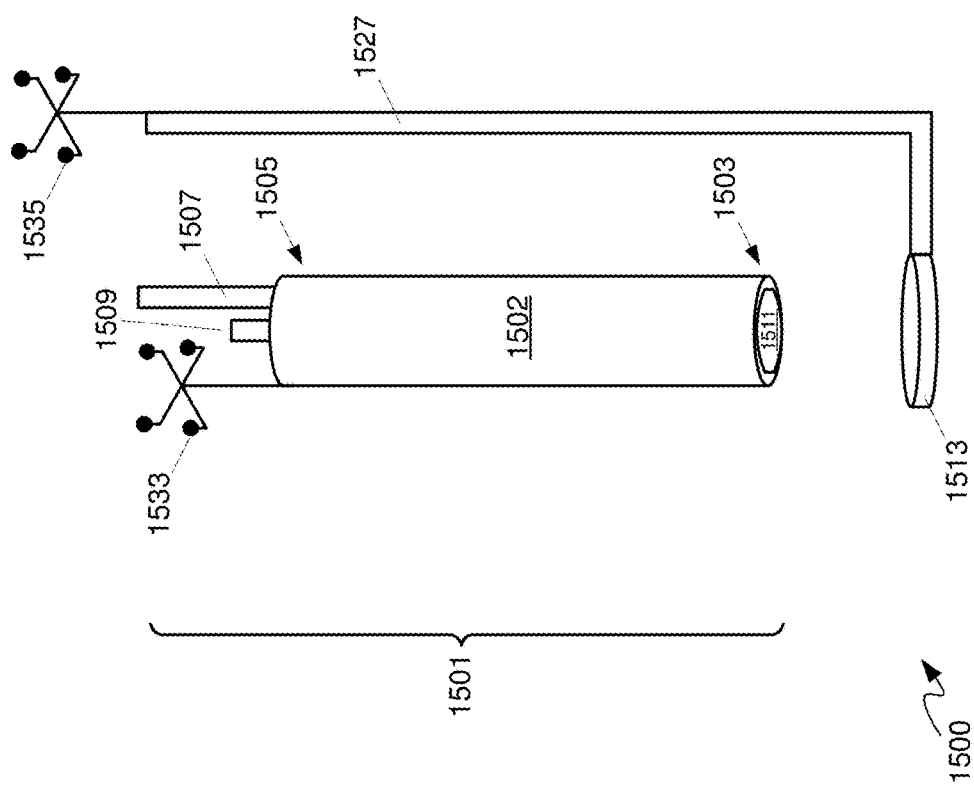

FIG. 14 depicts an OCT system that is in use with a surgical system and an access port FIG. 15 depicts an OCT system that includes a first tracking device located at proximal end of the OCT probe and a second tracking device located at a respective proximal end of handle connecting to the transparent material.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
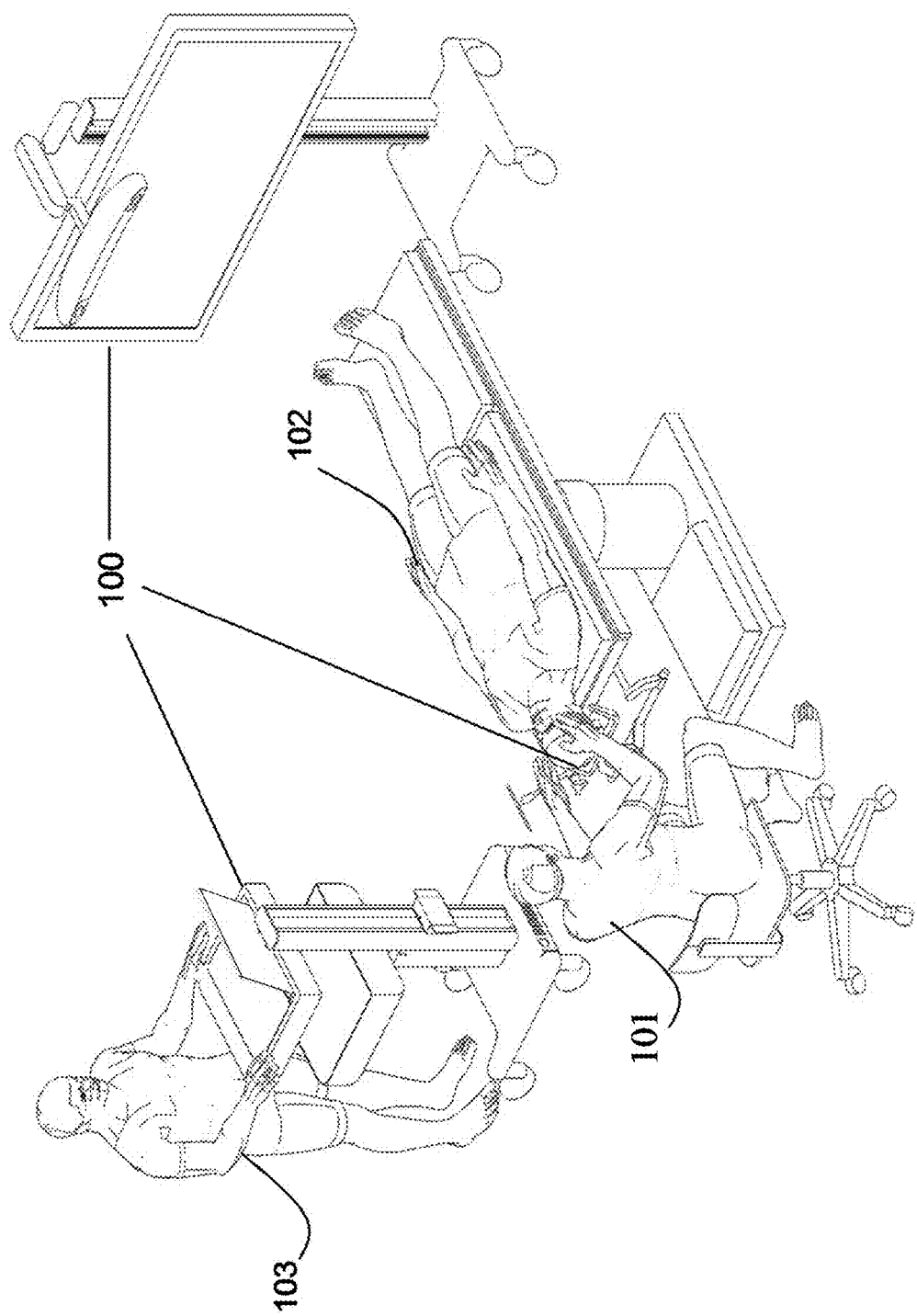
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
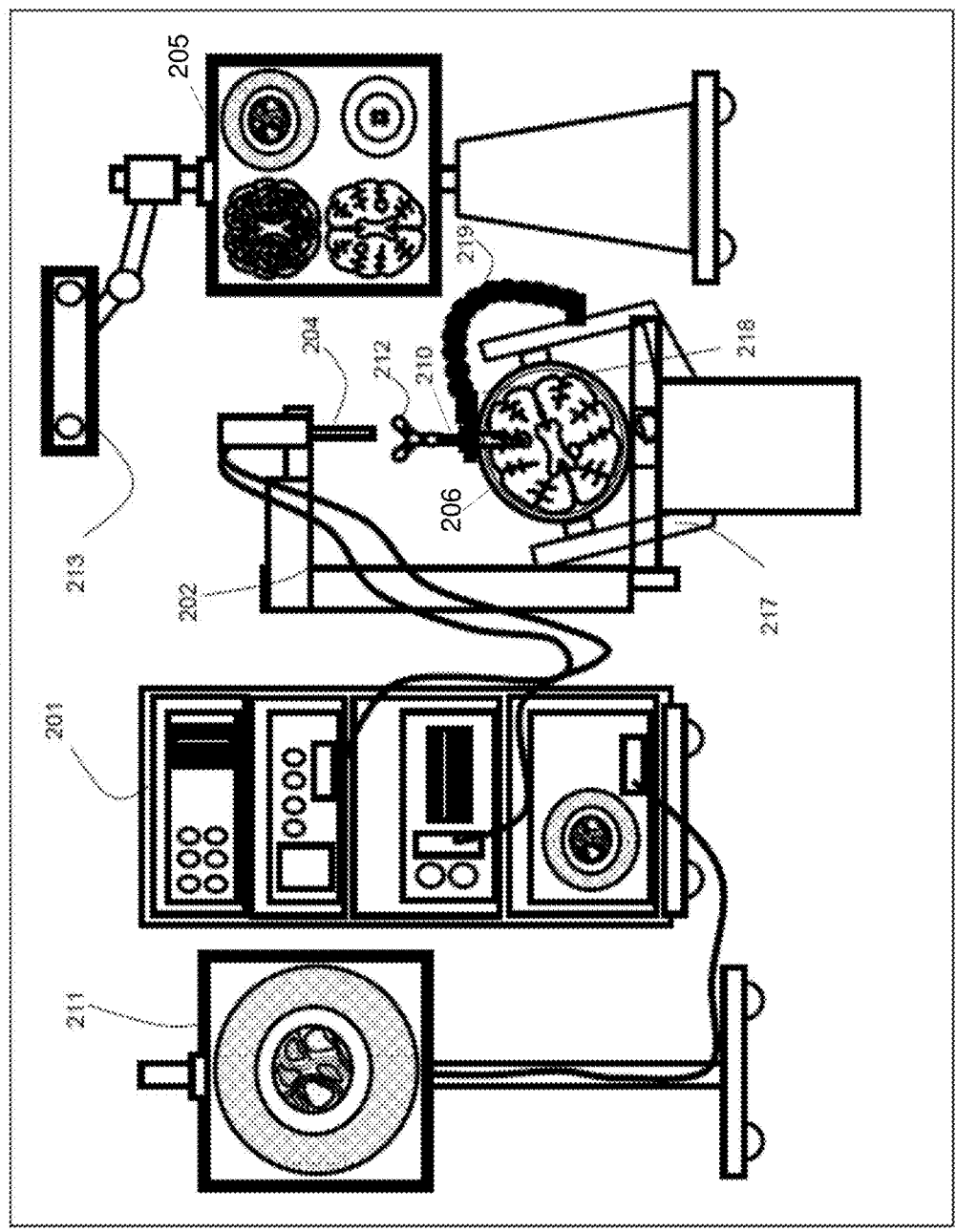
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
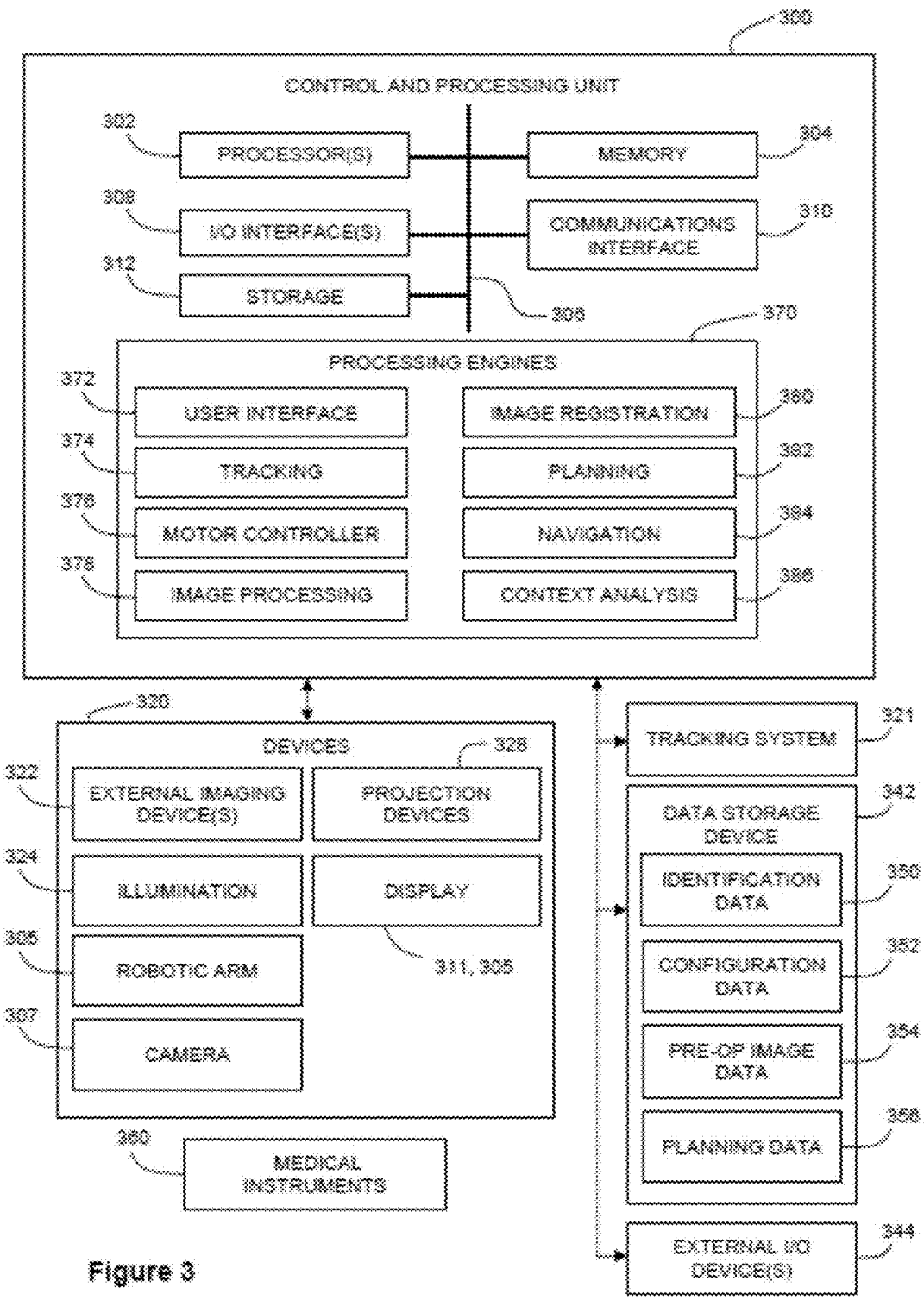
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
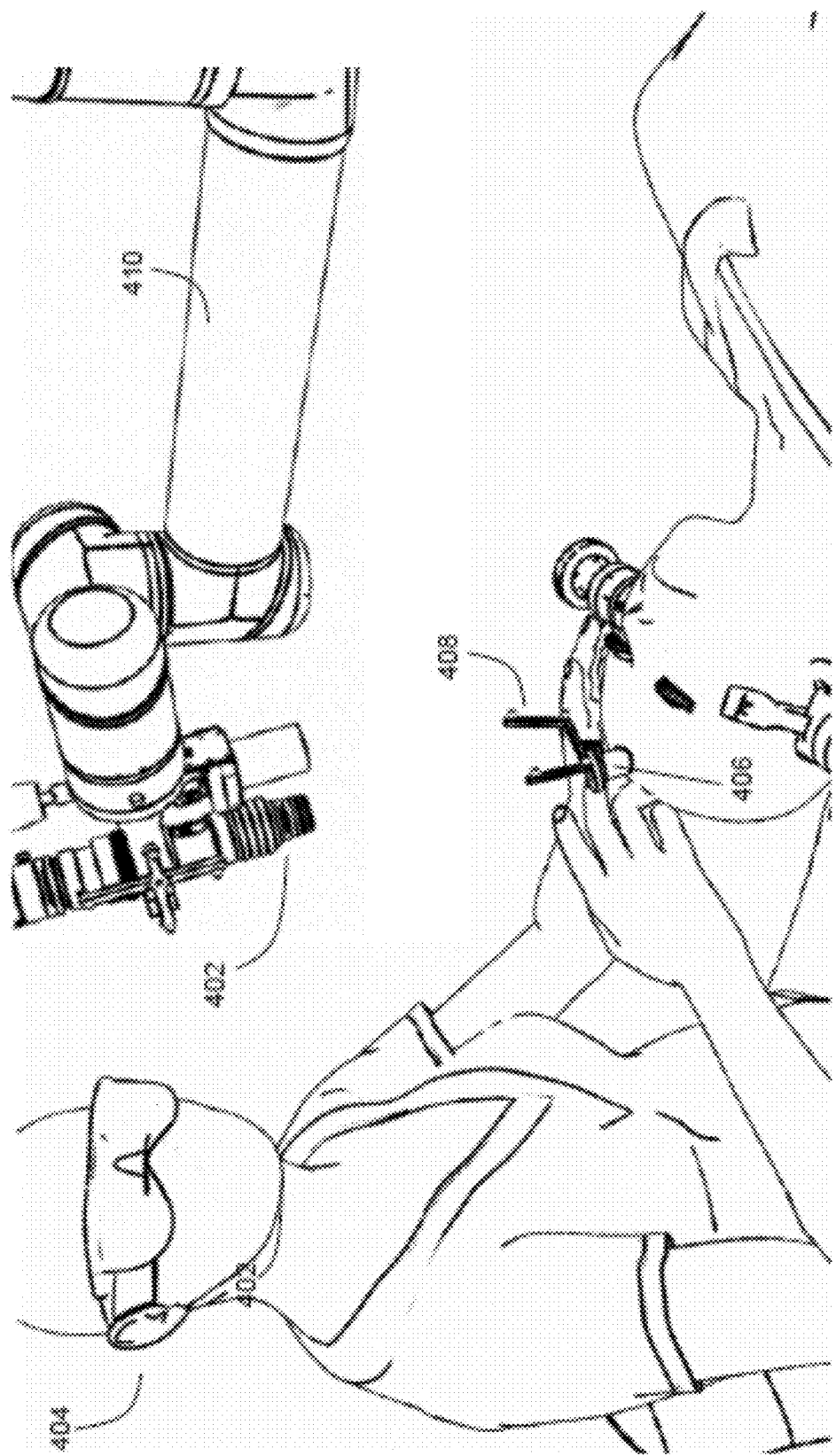
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
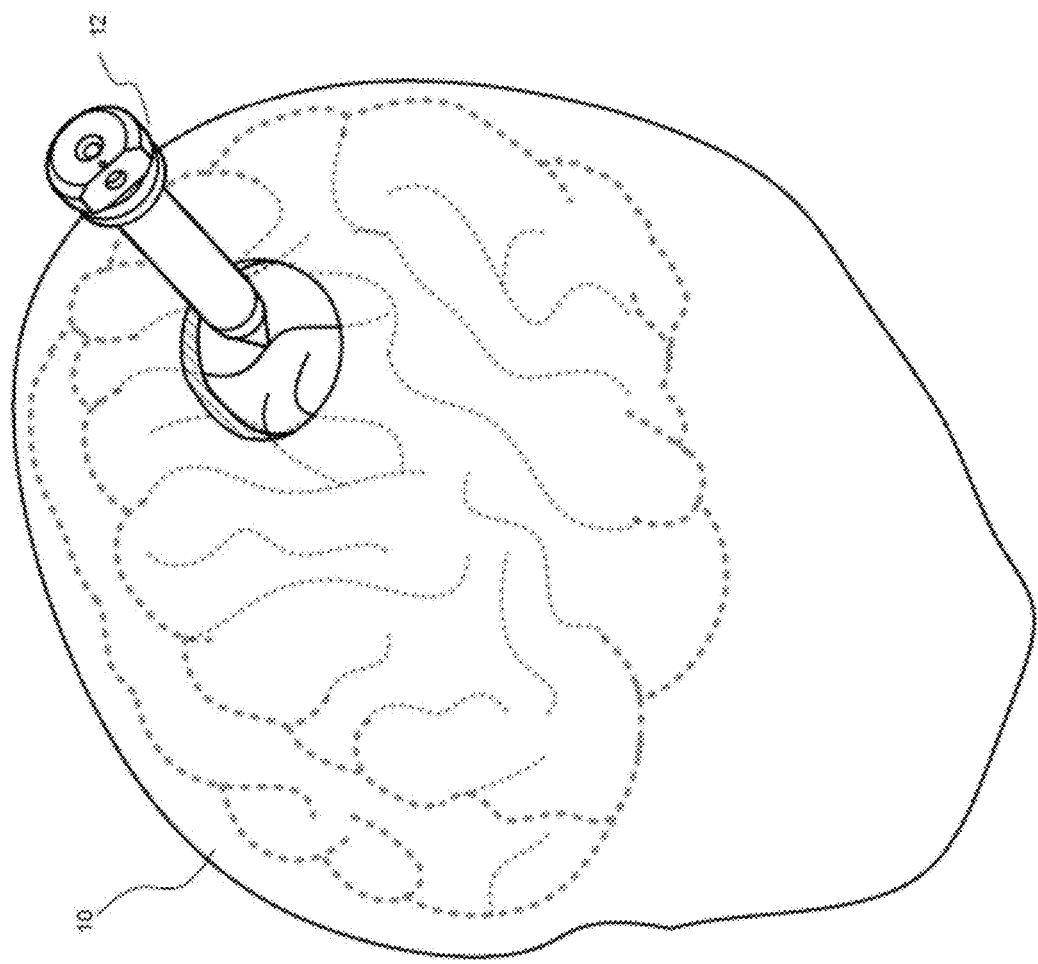
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Attention is next directed to FIG. 6, which depicts an example of a surgical tool that could be inserted through access port 12.

Specifically, FIG. 6 depicts an optical coherence tomography (OCT) system 600 comprising: an OCT probe 601 comprising: a body 602 having a distal end 603 and a proximal end 605; a positioner adapter 607 located at proximal end 605; a connector 609 to an OCT analysis device, connector 609 located at proximal end 605; and, an OCT scan lens 611 located at distal end 603; and, a transparent material 613 configured to planarize tissue at a scan plane of OCT scan lens 611. As described in further detail below.

The terms proximal end and distal end are used as, when OCT probe 601 is in use, proximal end 605 will be proximal a surgeon and the like, and distal end 603 will be distal the surgeon, and the like.

OCT probe 601 is generally configured to perform an OCT scan on tissue planarized by transparent material 613; for example, in use, body 602 of OCT probe 601 can be inserted through an access port, such as access port 12, connector 609 is connected to an OCT analysis device and/or OCT light source, and tissue planarized by transparent material 613 is scanned using OCT scan lens 611, in conjunction with the OCT analysis device coupled to OCT probe 601 using connector 609.

While body 602 is generally depicted as cylindrical, body 602 may generally comprise a size, shape and/or configuration which enables body 602 to be inserted through a surgical access port. Specifically, body 602 may be configured for insertion through a surgical port configured for corridor based surgery, such as access port 12. As such, positioner adapter 607 may comprise a handle configured to be held by a human hand, and may hence include grips, indentations, and the like for ergonomic use with a human hand; alternatively, positioner adapter 607 may be configured to be held by an arm of a device positioner, for example a component of a surgical system, such that the arm may position OCT system 600 in relation to a patient being operated on, for example in relation to, and/or through, an access port and/or a surgical port. In other words, OCT system 600 may be held in place manually using positioner adapter 607, and/or positioner adapter 607 may be configured to be held by an arm of a surgical system. Hence, positioner adapter 607 is depicted schematically, but a shape, configuration, and/or size of positioner adapter 607 may be adapted for a holding device with which positioner adapter 607 is to be used (e.g. a hand of a user and/or an arm of a surgical system); furthermore, positioner adapter 607 may comprise fasteners, apertures, and the like, configured to attach positioner adapter 607 to an arm of a surgical system.

OCT scan lens 611 is generally configured to focus and scan OCT light across tissue, as well as to collect light reflected from the tissue. OCT scan lens 611 may be a component of an OCT scan head located within body 602. Indeed, body 602 may include an OCT scan head that comprises OCT scan lens 611, and may further comprise one or more scanning components, including, but not limited to, a MEMS (microelectromechanical) mirror and a galvanometer, such scanning components configured to scan OCT light across a line and/or an area to obtain a two or three dimensional OCT image respectively. The OCT light may comprise laser light. Such OCT light from an OCT light source may be directed to the OCT scan lens 611 through connector 609. Further, the connector 609 may direct light from OCT scan lens 611 to an OCT detector and/or an OCT analysis device. Hence, connector 609 is generally configured for connection to the OCT analysis device, and/or an OCT light source (which may be located at the OCT analysis device), and hence connector 609 generally comprises an optical connector, for example to any suitable combination of optical fibers, light guides and the like which in turn connect to the OCT analysis device, and/or the OCT light source.

An OCT analysis device may comprise a light source, an optical coupler and/or beam splitter, and a reference arm which may comprise at least a reference mirror, and a detector. The light source may be directed to an optical coupler and/or beam splitter which splits the OCT light (e.g. laser light) into the reference arm and a sample arm. In the reference arm, the OCT light is directed to a mirror that sets a reference imaging distance from optical coupler and/or beam splitter. The OCT light then reflects back to the optical coupler and/or beam splitter. In the sample arm, the optical coupler and/or beam splitter may directs the OCT light to connector 609 which directs the OCT light to OCT scan lens 611 so that tissue is scanned. The reflected light from the tissue is received through OCT scan lens 611, which and which travels back through body 602 to the optical coupler and/or beam splitter through the connector 609. The reflected light from the tissue and the reference mirror then interferes and forms a fringe pattern which creates an A-scan OCT signal through Fourier transform.

As such, body 602 may further comprise any combination of free space optics, including, but not limited to, lenses, mirrors, light guides, diffusers, gratings, polarization optics, such as polarizers and wave plates, integrated optics, fiber optics, optical devices such as interferometers and the like, the free space optics configured to communicate light between connector 609 and OCT scan lens 611. Indeed, in some implementations, body 602 may include at least a portion of an OCT analysis device. For example, body 602 may include an interferometer, a reference arm, and/or photodetectors. In some implementations, body 602 may comprise one or more motors for moving and/or positioning OCT scan lens 611 during an OCT scan of tissue, such that OCT scans across a planarized scan area of the tissue, proximal transparent material 613. However, in other implementations, such scanning may occur by controlling angles of incidence and/or etendue of the OCT scan light from the OCT light source.

Furthermore, while body 602 is described as receiving OCT light using connector 609, conveying the OCT light to tissue, and collecting and conveying reflected OCT light to an OCT analysis device using connector 60, with production of OCT light and analysis of reflected OCT being external to OCT system 600, in other implementations, body 602 may comprise components configured to generate OCT light (e.g. an OCT light source) and/or optical and/or computing components configured to perform at least a pre-analysis of reflected OCT light prior to communicating with an OCT analysis device. Indeed, in some implementations, connector 609 may include, but is not limited to, a data and/or electrical connector. Hence, connector 609 may comprise a combination of an optical connector, a data connector and/or an electrical connector, configured to communicate optically, and/or electrically with components external to OCT system 600.

OCT scan lens 611 is generally configured to perform an OCT scan on tissue, and specifically configured to focus and/or scan OCT light onto tissue at a given distance from OCT scan lens 611, for example at a focal length of OCT scan lens 611, and the like. An OCT signal (e.g. reflected OCT light) is collected and conveyed to an OCT analysis device using connector 609. The OCT analysis device produces an OCT image of tissue being scanned, and the image may be rendered on a display device that may be a component of a surgical system, for example one or more projection devices 328, and/or one or more displays 305, 311 When tissue being scanned using OCT scan lens 611 is uneven, and specifically, when the tissue being scanned causes negative and positive time delays in an OCT signal, OCT images may be produced around a zero time delay line, which causes mirror artifacts in the OCT images. Transparent material 613 may lead to a reduction in such mirror images, as described hereafter.

Furthermore, as transparent material 613 planarizes tissue, such planarization may provide a visual indication of the area to be scanned, which may obviate use of a laser, a visible light source and the like for indicating the OCT scan area. In other words, as OCT light may not be visible to a human eye and/or an eye of a user, the planarized tissue may provide an indication of the area to be scanned.

As depicted, transparent material 613 comprises a transparent disc of material used to planarize tissue at a scan plane of OCT scan lens 611. For example the transparent material may comprise glass and/or the transparent material may comprise plastic and/or the transparent material may comprise any other transparent material compatible with surgery and that may be used to planarize tissue, including, but not limited to, transparent metal oxides. Specifically, transparent material 613 is substantially transparent to light used in optical coherence tomography. Furthermore, a tissue-facing side of transparent material 613 is substantially flat, and generally parallel to a scan plane of OCT scan lens 611.

Indeed, in use, transparent material 613 is pressed against tissue to planarize the tissue. Hence, transparent material 613 is generally of a stiffness and/or a hardness which will cause transparent material 613 to maintain its shape (i.e. not deform) when pressure is applied thereto, and transparent material 613 is pressed against tissue.

Furthermore, while transparent material 613 is depicted as a disc in FIG. 6, transparent material may be other shapes, for example, square, rectangular, triangular, octangular, etc. However, transparent material 613 of a size which includes the scanning area of OCT scan lens 611.

As depicted, OCT system 600 further comprises space between transparent material 613 and OCT scan lens 611. For example, a thickness of transparent material 613 may be selected to balance transparency of transparent material 613 with structural integrity of transparent material 613 when pressure is being applied to tissue, as described below, and space is provided between transparent material 613 and OCT scan lens 611 to minimize absorption of OCT light by transparent material 613.

As transparent material 613 does not extend to OCT scan lens 611, as depicted in FIG. 6, OCT system 600 further comprises an offset device 615 configured to maintain an offset distance between OCT scan lens 611 and transparent material 613. For example, as depicted, offset device 615 comprises a frame configured to hold transparent material 613 at the offset distance. In general, an offset distance is a distance which locates a tissue-facing side of transparent material 613 at the OCT scan distance from OCT scan lens 611. The OCT scan distance may be about the focal length of OCT scan lens 611. Hence, a distance between OCT scan lens 611 and the scan plane comprises the OCT scan distance.

Furthermore, as depicted the frame is attached to distal end 603, extends from distal end 603 and holds transparent material 613 at the offset distance, as described above. Offset device 615 and/or the frame may comprise metal, plastic, carbon fiber, and the like, and/or any material which may translate pressure applied to body 602 to transparent material 613 so that transparent material 613 is pressed against tissue to planarize it.

For example, attention is next directed to FIG. 7, which depicts a portion of OCT system 600 in use with tissue 701, which is uneven and, scanned without tissue 701 being planarized by transparent material 613, may cause mirror artifacts. However, as depicted, pressure is applied OCT system 600, which translates through body 602, to offset device 615 and to transparent material 613, which results in pressure 703 being applied transparent material 613 and hence on tissue 701 at a tissue-facing side of transparent material 613. Such pressure 703 results in tissue 701 at a tissue-facing side of transparent material 613 being compressed and hence planarized.

For example, in some implementations, OCT system 600 may be mounted to a device positioner and/or surgical arm that may be moved, for example robotically, and the surgical arm may be used to position OCT system 600 on an area of interest of tissue, for example, tissue of interest to a surgeon. The arm of the surgical system may be generally configured to position body 602 relative to tissue 701. The surgical arm may move OCT system 600 so that pressure is applied to tissue 701 and transparent material 613 planarizes tissue 701, which also indicates to a surgeon an area of tissue 701 to be scanned using OCT system 600. As described above, a distance between OCT scan lens 611 and the scan plane comprises an OCT scan distance, which is held at a fixed value using offset device 615; hence the surgical arm may move OCT scan lens 611 to point to an area of interest on tissue 701, while keeping OCT scan lens 611 at the fixed offset distance. This keeps an OCT image of tissue 701 generally flat. Hence, using offset device 615 to maintain the working distance between a sample and scan lens 611, a tissue of interest may be placed into axial imaging range of scan lens 611 for an OCT scan by a surgeon, and the like.

It is further apparent from FIG. 7 that a tissue-facing side of transparent material 613 is generally flat and about parallel to a scan plane of OCT scan lens 611 and/or normal to OCT scan lens 611. Hence, not only is tissue 701 planarized by transparent material 613, but tissue 701 is planarized in a scan plane of OCT scan lens 611.

Such planarization may lead to reductions in mirror artifacts in OCT images. For example attention is directed to FIG. 8, which depicts two OCT images "A" and "B". In OCT image "A", tissue being scanned was not planarized, and hence has a mirror artifact 801 (also highlighted with arrows). In OCT image "B", the same tissue was scanned with a prototype of OCT system 600, and was hence planarized as in FIG. 7; as such, in OCT image "B", mirror artifact 801 has been reduced and/or eliminated in comparison with OCT image "A".

Attention is next directed to FIG. 9, which depicts an alternative implementation of an OCT system 900, which is substantially similar to FIG. 9, with like elements having like numbers, however in a "900" series, rather than a "600" series. For example, OCT system 900 comprises: an OCT probe 701 comprising: a body 902 having a distal end 903 and a proximal end 905; a positioner adapter 907 located at proximal end 905; a connector 909 to an OCT analysis device, connector 909 located at proximal end 905; and, an OCT scan lens 911 located at distal end 903; and, a transparent material 913 configured to planarize tissue at a scan plane of OCT scan lens 911. Furthermore, OCT system 900 comprises an offset device 915.

In contrast to OCT system 600, however, OCT system 900 further comprises one or more of an immersion material and an index matching material 917 on a tissue-facing side of transparent material 913, the one or more of immersion material and index matching material 917 configured to optically couple transparent material 913 to the tissue. For example, or more of immersion material and index matching material 917 may comprise an optical coating which has an index of refraction that is intermediate an index of refraction of transparent material 913 and tissue to be scanned using OCT scan lens 911. Alternatively, one or more of immersion material and index matching material 917 may comprise a material which acts as one or more of an optical and physical interface between tissue to be scanned and transparent material 913. Either way, one or more of an immersion material and index matching material 917 is also substantially transparent to light used in optical coherence tomography and furthermore does not change the planarization of the tissue by transparent material 913. In other words, one or more of an immersion material and index matching material 917 is also substantially flat and substantially parallel to a tissue-facing side of transparent material 913.

One or more of immersion material and index matching material 917 may also reduce reflections of OCT light from a tissue-facing side of transparent material 913. Specifically, one or more of immersion material and index matching material 917 may comprise an anti-reflection coating on transparent material 913. Hence, in some implementations, an OCT scan lens-facing side of transparent material 913 may comprise an anti-reflection coating.

Attention is next directed to FIG. 10, which depicts an alternative implementation of an OCT system 1000, which is substantially similar to FIG. 10, with like elements having like numbers, however in a "1000" series, rather than a "600" series. For example, OCT system 1000 comprises: an OCT probe 1001 comprising: a body 1002 having a distal end 1003 and a proximal end 1005; a positioner adapter 1007 located at proximal end 1005; a connector 1009 to an OCT analysis device, connector 1009 located at proximal end 1005; and, an OCT scan lens 1011 located at distal end 1003; and, a transparent material 1013 configured to planarize tissue at a scan plane of OCT scan lens 1011.

However, in contrast to OCT system 600, transparent material 1013 extends between OCT scan lens 1011 and the scan plane of OCT scan lens 1011. In other words, as depicted transparent material 1013 comprises a frustum of transparent material between OCT scan lens 1011 and the scan plane of OCT scan lens 1011, though in other implementations transparent material 1013 may be other shapes, for example cylindrical and/or having a longitudinal shape similar to body 1002. While such implementations may result in some absorption of OCT light as compared to OCT system 600, OCT system 1000, may have increased structural integrity due to the lack of space between OCT scan lens 1011 and the scan plane of OCT scan lens 1011, as pressure is translated directly from body 1002 to transparent material 1013 without the use of an intervening offset device and/or frame. However, OCT system 1000 could include an optional frame to assist with translating pressure from body 1002 to a tissue-facing side of transparent material 1013 and/or to attach transparent material 1013 to distal end 1003.

Furthermore, a side of transparent material 1013 adjacent OCT scan lens 1011 may be adapted for a shape of OCT scan lens 1011 and/or be complementary to OCT scan lens 1011, to eliminate and/or reduce space and/or reflecting surface between transparent material 1013 and OCT scan lens 1011. In some implementations, optical epoxy and the like may be used to attach transparent material 1013 to OCT scan lens 1011, which may result in reduction and/or elimination of space there between. In other implementations, a fusion splicer can be used to fuse or weld two optical elements together though an electric arc.

Attention is next directed to FIG. 11, which depicts an alternative implementation of an OCT system 1100, which is substantially similar to FIG. 11, with like elements having like numbers, however in a "1100" series, rather than a "600" series. For example, OCT system 1100 comprises: an OCT probe 1101 comprising: a body 1102 having a distal end 1103 and a proximal end 1105; a positioner adapter 1107 located at proximal end 1105; a connector 1109 to an OCT analysis device, connector 1109 located at proximal end 1105; and, an OCT scan lens 1111 located at distal end 1103; and, a transparent material 1113 configured to planarize tissue at a scan plane of OCT scan lens 1111. Furthermore, OCT system 900 comprises an offset device 1115 similar to offset device 615, but adapted for a shape of transparent material 1113.

Specifically, in contrast to OCT system 600, a side of transparent material 1113 facing OCT scan lens 1111 is at an angle to a surface of OCT scan lens 1111 and/or at an angle to the OCT scan plane and/or at an angle to a tissue-facing side of transparent material 1113. Put another way, transparent material 1113 comprises a wedge configured to reduce reflection from transparent material 1113. For example, with reference to FIGS. 6 and 9, as transparent material 913 comprises a disc, reflections from surfaces of the disc, which are generally normal to a respective OCT scan lens, may result in artifacts in OCT images, unless coated with an anti-reflection coating as in some implementations of OCT system 900. However, configuring transparent material 1113 into a wedge, so that a side of transparent material 1113 facing OCT scan lens 1111 is at an angle to a surface of OCT scan lens 1111, may result in reduction in reflections from the side of transparent material 1113 facing OCT scan lens 1111, as OCT light is reflected away from OCT scan lens 1111.

Attention is next directed to FIG. 12, which depicts an alternative implementation of an OCT system 1200, which is substantially similar to FIG. 12, with like elements having like numbers, however in a "1200" series, rather than a "600" series. For example, OCT system 1200 comprises: an OCT probe 1201 comprising: a body 1202 having a distal end 1203 and a proximal end 1205; a positioner adapter 1207 located at proximal end 1205; a connector 1209 to an OCT analysis device, connector 1209 located at proximal end 1205; and, an OCT scan lens 1211 located at distal end 1203; and, a transparent material 1213 configured to planarize tissue at a scan plane of OCT scan lens 1211. Furthermore, OCT system 1200 comprises an offset device 1215.

However, in contrast to OCT system 600, OCT system 1200 further comprises a tracking device 1223 located at proximal end 1205, tracking device 1223 configured to be tracked by a navigation system external to OCT system 1200. While not depicted OCT system 1200 may further comprise a mount configured to removabley attach tracking device 1223 at proximal end 1205. Tracking device 1223 may provide a position of OCT system 1200 in three dimensional space, and hence OCT system 1200 may to be positioned relative to other tracked devices including other surgical tools such as an access port or a pointer. Tracking device 1223 is generally to extend away from body 1202 so that a camera, and the like, of a surgical navigation system may track a position of tracking device 1223 and hence a position of OCT system 1200, for example in an access port. As depicted, tracking device 1223 comprises four reflective spheres arranged in a configuration where each sphere is located at about a corner of a square. However, other numbers of spheres and other configurations are within the scope of present implementations. In particular, one or more of a number, arrangement, and configuration of such spheres may be selected to provide a given tracking accuracy, including, but not limited to, a tracking accuracy that is less than about half a diameter of a sensing array surface. However, tracking device 1223 may include tracking devices other than reflective spheres. For example, in some implementations, tracking device 1223 may include a flexible sheath configured to measure tip position deflection, for example deflection of a tip of the flexible sheath.

Attention is next directed to FIG. 13, which depicts an alternative implementation of an OCT system 1300, which is substantially similar to FIG. 6, with like elements having like numbers, however in a "1300" series, rather than a "600" series. For example, OCT system 1300 comprises: an OCT probe 1301 comprising: a body 1302 having a distal end 1303 and a proximal end 1305; a positioner adapter 1307 located at proximal end 1305; a connector 1309 to an OCT analysis device, connector 1309 located at proximal end 1305; and, an OCT scan lens 1311 located at distal end 1303; and, a transparent material 1313 configured to planarize tissue at a scan plane of OCT scan lens 1311. However, in contrast to OCT system 600, where OCT probe 601 and transparent material 613 are integrated using offset device 615, in OCT system 1300, OCT probe 1301 and transparent material 1313 are discrete components (i.e. separate from one another). Furthermore, OCT system 1300 further comprises a handle 1327 attached to the transparent material, handle 1327 configured to extend through a surgical port.

For example, attention is next directed to FIG. 14 which schematically depicts OCT system 1300 in use with a surgical system 1400 comprising: a device positioner 1401 that includes a coupler 1403 configured to couple to positioner adapter 1307 (not visible in FIG. 14) of OCT probe 1301, as depicted; an access port 1412, similar to access port 12, an OCT analysis device 1413 that, as depicted, includes an OCT light source, OCT analysis device 1413 in communication with OCT probe 1301 via an optical fiber and/or an electrical cable 1415, and the like, coupled to connector 1309; a computing device 1420 in communication with OCT analysis device 1413; and a display device 1427 configured to render images, including, but not limited to OCT images 1429.

In particular, access port 1412 is inserted into a patient, as in FIG. 5, so that tissue 701 is accessible; further access port 1412 then provides a corridor to interact with tissue 701. Device positioner 1401, that may include a robotic arm, is controlled to position OCT probe 1301 relative to access port 1412 so that OCT probe 1301 may perform an OCT scan on tissue 701: for example, computing device 1420 may be in communication with device positioner 1401 and control device positioner 1401, so that a OCT scan lens 1311 of OCT probe 1301 is at an offset distance from tissue 701. In particular, OCT probe 1301 is not physically inserted through access port 1412 in these configurations but is configured to perform an OCT scan through access port 1412, but at a distance from a proximal end of access port 1412 (i.e. a proximal end of access port 1412 is towards a surgeon and the like while a distal end of access port 1412 is towards tissue 701.

A surgeon, and the like, as represented by hand 1331, manually inserts transparent material 1313 through access port 1412 using a proximal end of handle 1327 and applies pressure to transparent material 1313 so that tissue 701 adjacent a tissue-facing side of transparent material is planarized.

OCT probe 1301 is used to perform the OCT scan while transparent material 1313 is planarizing tissue 701, and OCT analysis device 1413 may Computing device 1420 received OCT data from OCT analysis device 1413, processes the OCT data to produce an OCT image 1429 and controls display device 1427 to render OCT image 1429 (as depicted, similar to image "B" in FIG. 8).

As OCT scanning and data collection may occur in real time, OCT image 1429 may be updated in real time; hence the surgeon, and the like, may move transparent material 1313 to both apply pressure and change an angle of transparent material 1313 until a mirror artifact is eliminated and/or is reduced in image 1429.

Hence, in contrast to OCT system 600, in OCT system 1300, OCT probe 1301 and transparent material 1313 are discrete components. Furthermore, OCT system 1300 further comprises handle 1327 attached to transparent material 1313, handle 1327 configured to extend through a surgical port, including, but not limited to access port 1412. In addition, at least a proximal end of handle 1327 is is configured to be held by a human hand, such as hand 1331. A distal end of handle 1327 may be attached to transparent material 1313 using one or more frames, one or more connectors, epoxy, and the like and may have a shape and/or configuration and/or dimensions compatible with: insertion of transparent material 1313 through access port 1412; and a proximal end of handle 1327 extending through access port 1412 such that transparent material 1313 may be manipulated (e.g. pressure placed on tissue 701 such that tissue 701 is planarized by transparent material 1313) by hand 1331 external to access port 1412.

While not depicted, it is appreciated that transparent material 1313 may include one or more of an immersion material and an index matching material on a tissue-facing side of transparent material 1313 and/or transparent material 1313 may be wedge shaped and/or transparent material may be a shape other than disc, as depicted, as long as a tissue-facing side of transparent material 1313 is substantially flat. In other words, alternative implementations of transparent material described with reference to FIGS. 9, 10 and 11 may also be implemented at transparent material 1313, as well as combination thereof.

Attention is next directed to FIG. 15, which depicts an alternative implementation of an OCT system 1500, which is substantially similar to FIG. 13, with like elements having like numbers, however in a "1500" series, rather than a "1300" series. For example, OCT system 1500 comprises: an OCT probe 1501 comprising: a body 1502 having a distal end 1503 and a proximal end 1505; a positioner adapter 1507 located at proximal end 1505; a connector 1509 to an OCT analysis device, connector 1509 located at proximal end 1505; and, an OCT scan lens 1511 located at distal end 1503; and, a transparent material 1513 configured to planarize tissue at a scan plane of OCT scan lens 1511. OCT system 1500 further comprises a handle 1527 attached to transparent material 1513, similar to handle 1327.

However, in contrast to OCT system 1300, OCT system 1500 further comprises a first tracking device 1533 located at proximal end 1505, first tracking device 1533 similar to tracking device 1223. In addition, OCT system 1500 further comprises a second tracking device 1535 located at a respective proximal end of handle 1527, tracking device 1535 configured to be tracked by a navigation system. As depicted, second tracking device 1535 is also similar to tracking device 1223. Hence, a navigation system may track a position of both OCT probe 1501 and transparent material 1513 (presuming a physical configuration of transparent material 1513 and handle 1527 has been provided to the navigation system). In these implementations, a surgeon and the like may position transparent material 1500 onto a tissue of interest through the use of handle 1527 using a surgeon's hand, and the like. Tracking device 1535 located at handle 1527 then provides the navigation system with a position of transparent material 1513. At the same time, the navigation system may detects a position of OCT probe 1501 using tracking device 1533. Device positioner 1401 may be used obtain the two three-dimensional position information (e.g.

positions of each of tracking devices 1533, 153) and automatically position OCT probe 1501 at a fixed distance away from transparent material 1513 (e.g. the working distance of scan lens 1511) for OCT scanning. Since, in these implementations, the positioning process of OCT probe 1501 can be automatic through the use of the navigation system and device positioner 1401, OCT probe 1501 may follow transparent material 1513 and keep the tissue of interest in focus and within the imaging area of OCT probe 1501, for example when transparent material 1513 is placed on to the tissue. Hence, OCT system 1500 may provide both auto-positioning and an auto-focusing feature. In addition, in some implementations, OCT system 1500 may comprise one of first tracking device 1533 and second tracking device 1535, but not the other of first tracking device 1533 and second tracking device 1535.

While features of OCT systems and probes are described with reference to specific implementations, features described with reference to one implementation of an OCT system and/or probe may be used with other implementations of OCT systems and/or probes. For example, any of the OCT systems and/or probes described herein may be adapted to include anti-reflective coatings, immersion materials, index matching materials, tracking devices, and the like. Furthermore, while present implementattions have been described with reference to port-based surgery, present implementations may be used other types of surgery that is no port-based including, but not limited to open case surgery, open cranial surgery, and the like.

Described herein is are implement systems that include OCT systems and/or probes which planarize material in a scan plane of an OCT scan lens using a transparent material which may result in a reduction and/or elimination of mirror artifacts.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. An OCT (Optical Coherence Tomography) system comprising:
    an OCT probe having a proximal end and a distal end, the OCT probe comprising:
        a positioner adapter located at the proximal end;
        an OCT scan lens located at the distal end;
        a first tracking device located at the proximal end;
    a device comprising:
        a transparent material transparent to OCT light and configured to planarize tissue at a scan plane of the OCT scan lens;
        a handle attached to the transparent material and configured to: extend through a surgical port; and be held by a human hand to manipulate the transparent material independent of the OCT probe to place pressure on the tissue to planarize the tissue;
        a second tracking device located at a respective proximal end of the handle;
    an arm configured to hold the OCT probe using the positioner adapter; and
    a navigation system configured to: cause the arm to position the OCT probe relative to the transparent material to maintain focus at the planarized tissue as the navigation system tracks respective positions of the first tracking device and the second tracking device.

2. The OCT system of claim 1, wherein a tissue-facing side of the transparent material is substantially flat.

3. The OCT system of claim 1, further comprising an immersion material on a tissue-facing side of the transparent material, the immersion material configured to physically couple the transparent material to the tissue.

4. The OCT system of claim 1, further comprising an index matching material on a tissue-facing side of the transparent material, the index matching material configured to optically couple the transparent material to the tissue.

5. The OCT system of claim 1, wherein a side of the transparent material facing the OCT scan lens is at a non-zero angle to a surface of the OCT scan lens.

6. The OCT system of claim 1, wherein a distance between the OCT scan lens and the scan plane comprises an OCT scan distance.

7. The OCT system of claim 1, wherein the transparent material comprises glass.

8. The OCT system of claim 1, wherein the transparent material comprises plastic.

9. The OCT system of claim 1, wherein the arm is configured to position the OCT device relative to the tissue.

10. The OCT system of claim 1, wherein a body of the OCT device is configured for insertion through the surgical port.

11. The OCT system of claim 1, wherein a respective distal end of the handle is attached to the transparent material using at least one of: one or more frames; one or more connectors; and epoxy.

12. The OCT system of claim 1, wherein a respective distal end of the handle includes a 90° bend, the respective distal end of the handle attached to the transparent material.

13. The OCT system of claim 1, wherein the handle is further configured to: extend through the surgical port configured for corridor based surgery.

14. The OCT system of claim 1, wherein the OCT probe and the device are discrete components.

15. The OCT system of claim 1, wherein the OCT probe further comprises a connector to an OCT analysis device, the connector located at the proximal end of the OCT probe.

16. The OCT system of claim 1, wherein the OCT scan lens is configured to focus and scan the OCT light at the scan plane of the OCT scan lens.

* * * * *